(12) United States Patent
Vacher et al.

(10) Patent No.: US 7,902,381 B2
(45) Date of Patent: Mar. 8, 2011

(54) SYNTHESISING METHOD AND BENZOXATHIEPINE INTERMEDIATES

(75) Inventors: Bernard Vacher, Castres (FR); Yves Brunel, Marssac-sur-Tarn (FR); Florence Castan-Cuisiat, Castres (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 1186 days.

(21) Appl. No.: 11/547,708

(22) PCT Filed: Apr. 8, 2005

(86) PCT No.: PCT/FR2005/000859
§ 371 (c)(1),
(2), (4) Date: Oct. 6, 2006

(87) PCT Pub. No.: WO2005/103027
PCT Pub. Date: Nov. 3, 2005

(65) Prior Publication Data
US 2008/0234499 A1    Sep. 25, 2008

(30) Foreign Application Priority Data

Apr. 9, 2004 (FR) ...................................... 04 03760

(51) Int. Cl.
*C07D 327/02* (2006.01)
(52) U.S. Cl. ............. 549/10; 549/355; 560/17; 560/152; 562/431; 562/512
(58) Field of Classification Search .................... 549/10, 549/346, 355; 560/152, 17; 562/512, 431
See application file for complete search history.

(56) References Cited

U.S. PATENT DOCUMENTS

| 3,636,074 A | 1/1972 | Dachs et al. |
| 2004/0127552 A1 | 7/2004 | Vacher et al. |

FOREIGN PATENT DOCUMENTS

WO    WO-02/081464 A    10/2002

OTHER PUBLICATIONS

Roush, W. R. et al.; J. Org. Chem., vol. 52, No. 2, pp. 316-318 (1987).
Raghavan, S. et al.; J. Org. Chem. vol. 68, No. 12, pp. 5002-5005 (2003).
Mickel, S.J. et al.; Organic Process Research & Development, vol. 8, No. 1, pp. 92-100 (2004).
Huang, P-Q. et al.; Tetrahedon Letters, No. 42, pp. 9039-9041 (2001).
Chen,C. et al.; J. Org. Chem., vol. 68, No. 7, pp. 2633-2638 (2003).

*Primary Examiner* — Janet L Andres
*Assistant Examiner* — David E Gallis
(74) *Attorney, Agent, or Firm* — Birch, Stewart, Kolasch & Birch, LLP

(57) ABSTRACT

The invention relates to preparing derivatives of formula (1), wherein, in particular $R_1$ and $R_2$, identical or different, represent a hydrogen, flourine or chlorine atom, a hydroxy group, an alkyl radical and an alkoxy radical, $R_3$ is an alkyl radical, a hydroxy group, or a methoxy radical, $R_4$ is a hydrogen atom or a methyl radical and $R_5$ and $R_6$, identical or different, represent a hydrogen atom, an alkyl radical, an alkoxy radical, an alkylthio radical, and an alkylamino radical. The inventive method consists in reducing an amid of formula (9).

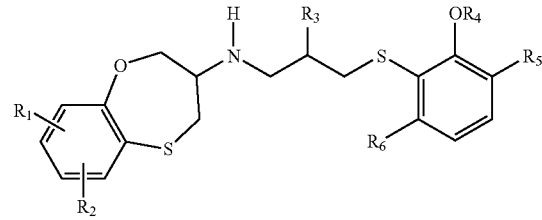

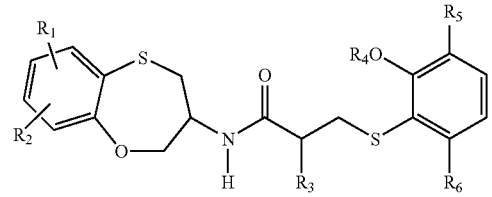

15 Claims, No Drawings

SYNTHESISING METHOD AND BENZOXATHIEPINE INTERMEDIATES

The present invention relates to a new method for preparing derivatives of benzoxathiepines of the general formula

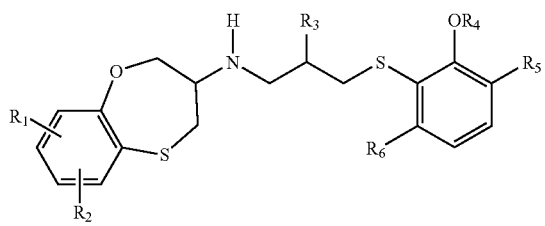

(1)

in which:

$R_1$ and $R_2$, identical or different, represent:

a hydrogen atom;

a fluorine atom or a chlorine atom;

a hydroxy group;

an alkyl radical, chosen from among the radicals methyl, ethyl, propyl, or isopropyl;

an alkoxy radical, chosen from among the radicals methoxy, ethyloxy, propyloxy, or isopropyloxy;

when groups $R_1$ and $R_2$ occupy adjacent positions on the aromatic ring, then $R_1R_2$ represents —$CH_2CH_2CH_2$—, —$OCH_2CH_2$—, —$OCH_2O$—, or —$CH_2CH_2O$—;

$R_3$ represents:

an alkyl radical, chosen from among the radicals methyl, ethyl, propyl, or isopropyl;

a hydroxy group or a methoxy radical;

$R_4$ represents:

a hydrogen atom or a methyl radical;

$R_5$ and $R_6$, identical or different, represent:

a hydrogen atom;

an alkyl radical, chosen from among the radicals methyl, ethyl, or isopropyl;

an alkoxy radical, chosen from among the radicals methoxy, ethyloxy, or isopropyloxy;

an alkylthio radical, chosen from among radicals methylthio, ethylthio, or isopropylthio;

an alkylamino radical, chosen from among the radicals N-methylamino or N,N-dimethylamino;

or $R_4R_5$ represents a radical chosen from among the radicals —$CH_2CH_2$—, —$CH_2O$—, —$CH_2CH_2O$—, —$CH_2CH_2S$—, —$CH_2CH_2NR_4$— and $R_6$ is as defined previously, their addition salts and the hydrates of these addition salts with mineral acids or pharmaceutically acceptable organic acids, as well as their tautomeric forms, enantiomers, mixtures of enantiomers and stereoisomers either pure or in a racemic mixture or not.

The new method, object of the present invention, applies more particularly to compounds of the formula (1a),

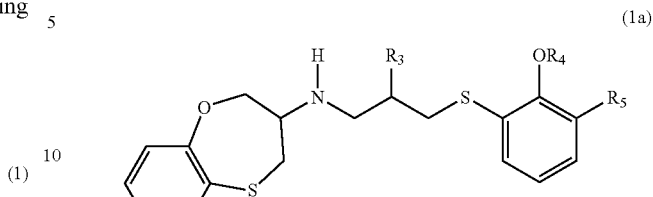

(1a)

in which:

$R_3$ represents an alkyl radical, chosen from among the radicals methyl, ethyl, or isopropyl, $R_4$ represents a hydrogen atom or a methyl radical, $R_5$ represents a hydrogen atom or a methyl radical;

or $R_4R_5$ represents a —$CH_2CH_2$— radical;

their addition salts and the hydrates of these addition salts with mineral acids or pharmaceutically acceptable organic acids, as well as their tautomeric forms, enantiomers, mixtures of enantiomers and stereoisomers either pure or in a racemic mixture or not.

In one embodiment of the invention, the preferred compounds of formula (1a) are:

N-{3-[(2-Methoxyphenyl)sulfanyl]-2-methylpropyl}-3,4-dihydro-2H-1,5-benzoxathiepin-3-amine;

2-{[3-(3,4-Dihydro-2H-1,5-benzoxathiepin-3-ylamino)-2-methylpropyl]sulfanyl}-6-methylphenol, their addition salts and the hydrates of these addition salts with mineral acids or pharmaceutically acceptable organic acids, as well as their tautomeric forms, enantiomers, mixtures of enantiomers and stereoisomers either pure or in a racemic mixture or not.

The new method applies to compounds of formula (1) and more particularly to those of formula (1a) in which the C(3) stereogenic carbon atom of the 3,4-dihydro-2H-1,5-benzoxathiepine fragment has a (R) absolute configuration and in which the stereogenic carbon atom that carries group $R_3$ has a (S) absolute configuration. The descriptors (R) and (S), used to specify the absolute configuration of the stereogenic atoms contained in formula (1) molecules, are defined by the Cahn-Ingold-Prelog priority rules (E. L. Eliel and S. H. Wilen, Stereochemistry of Organic Compounds, John Wiley & Sons, Inc., chap. 5, 104-12, 1994).

In another particularly advantageous embodiment of the invention, the formula (1a) compounds are chosen from among the following stereoisomers:

(3R)-N-{(2S)-3-[(2-Methoxyphenyl)sulfanyl]-2-methylpropyl}-3,4-dihydro-2H-1,5-benzoxathiepin-3-amine;

2-({(2S)-3-[(3R)-3,4-Dihydro-2H-1,5-benzoxathiepin-3-ylamino]-2-methylpropyl}sulfanyl)-6-methylphenol, their addition salts and the hydrates of these addition salts with mineral acids or pharmaceutically acceptable organic acids. In the present invention, stereoisomers are considered to be pure if they are associated with less than 1% of another stereoisomer of a mixture of stereoisomers (i.e., diastereoisomeric excess >98%, L'Actualite Chimique 2003, 11/12, 10-4).

The compounds of general formula (1) are described in the international patent application WO 02/081464 and are claimed to be useful in the treatment of stable angina, unstable angina, cardiac insufficiency, congenital long QT syndrome, myocardial infarction, and cardiac rhythm disturbances.

Formula (1) compounds can be synthesized according to the method described in WO 02/081464. However, the method in question presents several disadvantages:

it makes use of costly raw materials and reagents, some of which are potentially explosive;

whereas the total yield of formula (1) compounds is low, the quantity of by-products generated is considerable;

some of the synthesis steps are not reproducible.

Considering these disadvantages, the method described in WO 02/081464 is extremely difficult, even impossible, to carry out on a semi-industrial or industrial scale.

The object of the present invention precisely relates to a new method for the synthesis of formula (1) compounds and in particular those of formula (1a) that, contrary to those illustrated in WO 02/081464, are entirely capable of being carried out on a semi-industrial or industrial scale. Therefore, the method provided by the invention constitutes a major improvement compared to the prior method and provides a particularly advantageous approach to formula (1) compounds and in particular to those of formula (1a) whose therapeutic potential is significant.

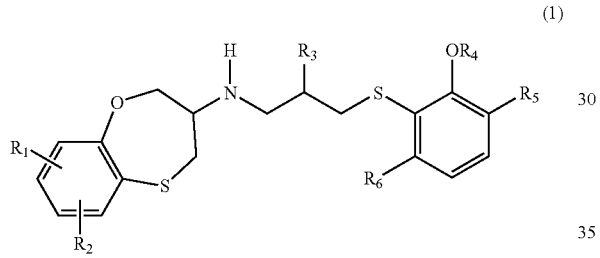
(1)

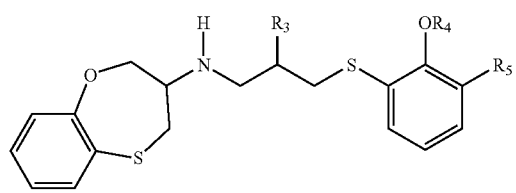
(1a)

A first aspect of the invention thus relates to the improvement of the method of synthesis of formula (1) compounds and more particularly those of formula (1a) by the reduction of a new intermediate of formula (9), respectively new intermediate (9a)

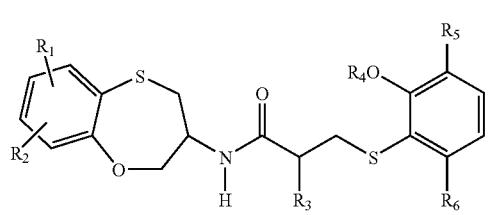
(9)

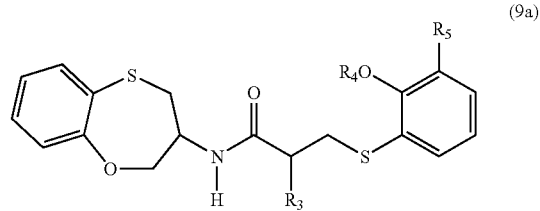
(9a)

preferably obtained by condensation of the compounds of formulas (5), (7), or (8)

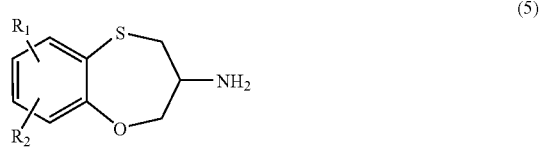
(5)

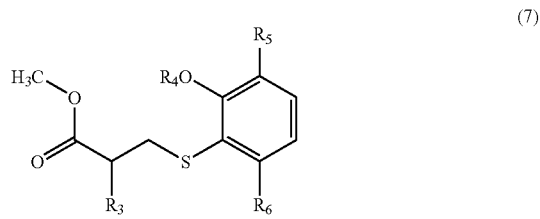
(7)

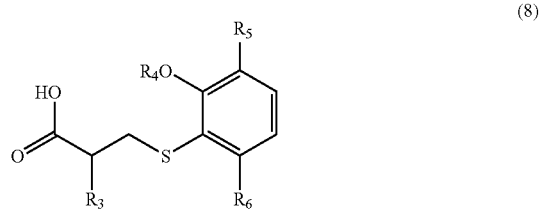
(8)

and more particularly by condensation of the compounds of formulas (5), (7a), or (8a)

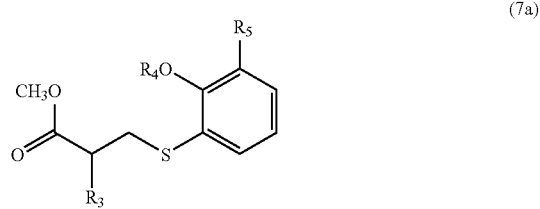
(7a)

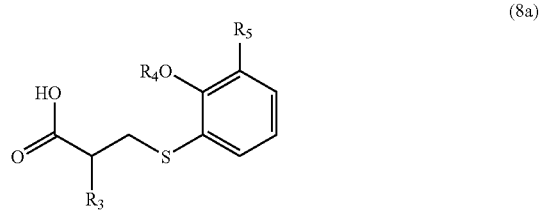
(8a)

in which radicals $R_1$, $R_2$, $R_3$, $R_4$, $R_5$, and $R_6$ have the meaning given with regard to formula (1) or, preferably, the meaning given with regard to formula (1a).

The preferred stereoisomer of the compounds of formulas (1), (1a), (9), and (9a) is, in all cases, that in which the stereogenic carbon atoms of the 3,4-dihydro-2H-1,5-benzoxathiepine fragment and of the propionamine/propionamide chain are of absolute configuration (R) and (S), respectively.

The present invention also relates to new intermediates of the synthesis of formula (9) and more particularly to those of formula (9a).

A second aspect of the invention comprises the improvement of synthesis methods of formula (5)

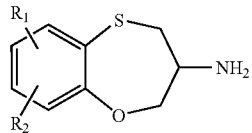
(5)

compounds in which radicals $R_1$ and $R_2$ have the meaning given with regard to formula (1)

according to which a formula (2) compound

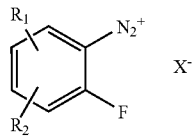
(2)

is treated with a cystine ester, preferably a L-cystine ester, to yield the formula (3) compound

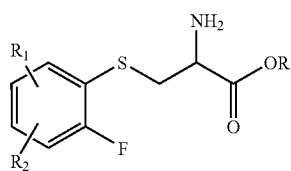
(3)

in which R represents a methyl radical, which by the reduction of at least one hydride-donating agent produces compound formula (4)

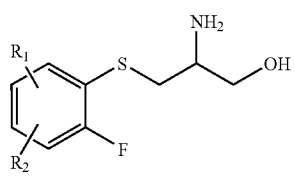
(4)

that is cyclized, chemoselectively, to yield the formula (5) compounds, in which $R_1$ and $R_2$ have the meaning given with regard to formula (1) or, preferably, the meaning given with regard to formula (1a). The preferred enantiomer of the compounds of formulas (3), (4), and (5) is, in all cases, that in which the stereogenic carbon atom is of absolute configuration (R).

This second aspect of the invention preferably comprises improvement in the method of synthesis of formula (5a) compound, analogue of compounds of formula (5) above for which $R_1$ and $R_2$ each represent a hydrogen atom, according to which the compounds of formulas (2a), (3a), and (4a), analogues of compounds of formulas (2), (3), and (4) respectively and for which $R_1$ and $R_2$ each represent a hydrogen atom, are used in the method described above for obtaining formula (5) compounds.

A third aspect of the invention includes the method of synthesis of new intermediates of formulas (7) and (8)

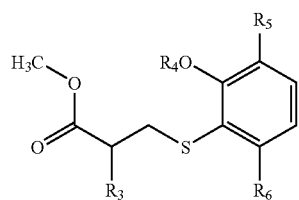
(7)

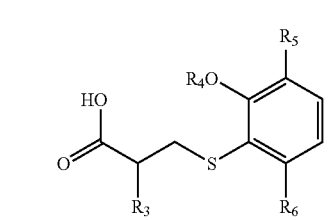
(8)

and more particularly new synthetic intermediates (7a) and (8a):

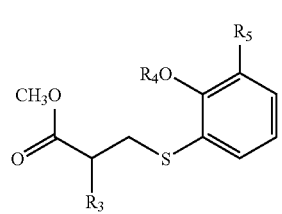
(7a)

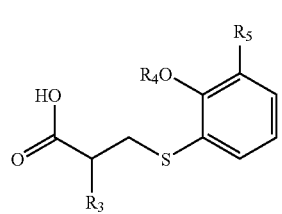
(8a)

in which the compound of a type methyl 3-[(methylsulfonyl)oxy]proponoate substituted in position 2, of formula (6)

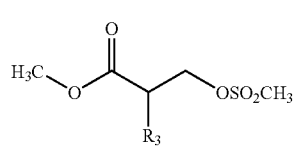
(6)

is treated with appropriate arylthiophenol in the presence of an organic base and/or mineral to yield the compound of formula (7), or more particularly (7a),

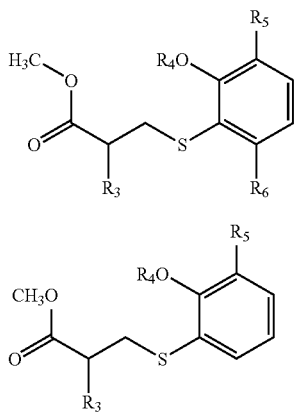

(7)

(7a)

that can be hydrolyzed in the acid corresponding to formula (8), or more particularly (8a)

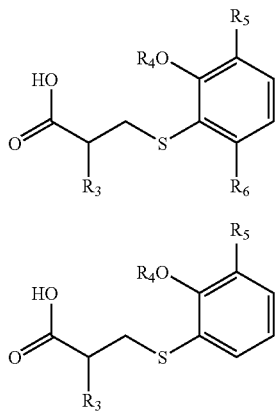

(8)

(8a)

in which groups $R_3$, $R_4$, $R_5$, and $R_6$ have the meaning given with regard to formula (1) or, preferably, the meaning given with regard to formula (1a). The preferred enantiomer of formula (6) compounds is that for which the stereogenic carbon atom is of absolute configuration (R), whereas the preferred enantiomer of compounds of formulas (7), (8), (7a), and (8a) is that for which the stereogenic carbon atom is of absolute configuration (S).

This third aspect of the invention also relates to compounds of formula (7), and more particularly (7a), with the exception of compounds for which $R_3$ represents a methyl radical while $R_4$, $R_5$, and $R_6$ each represent a hydrogen atom.

Indeed, U.S. Pat. No. 3,636,074 discloses such a compound. However, the compound disclosed in said U.S. patent is not prepared by a method analogous to the method provided by the present invention and it is not used as a synthetic intermediate in the preparation of benzoxathiepine.

In this third aspect, the invention also relates to compounds of formula (8), or more particularly to compounds of formula (8a).

The preparation method provided by the present invention, of compounds of general formula (1) and in particular those of formula (1a), is new, more economical, and more respectful of the environment that the previous method (WO 02/081464). Furthermore, contrary to the previous method, it can be carried out on a semi-industrial or industrial scale.

More specifically, according to the conditions of the previous technique (WO 02/081464), the compounds of formula (1) and in particular those of formula (1a) arise from a reductive amination reaction between the compound of formula (5) and the aldehyde of formula (A), cf. scheme I.

Scheme I

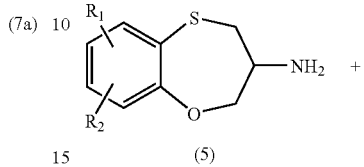

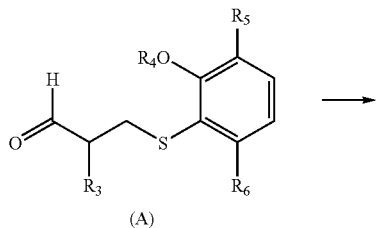

(A)

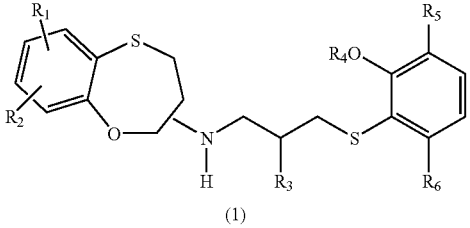

(1)

However, the aldehyde of formula (A), in particular when the radical $R_3$ represents a methyl group, is both chemically and stereochemically unstable; the instability of certain aldehydes of type (A) have already been reported, e.g., J. Org. Chem. 1987, 52 (2), 316-8; J. Org. Chem. 2003, 68 (12), 5002-5; Organic Process Research & Development 2004, 8(1), 92-100. Therefore, the formula (A) compound was prepared in a transitory fashion at a very low temperature (<-60° C.) then trapped, in situ, by means of the amine (5) and an excess of reducing agent. Even at a laboratory scale, the chemical yield obtained, as well as the stereochemical purity of compound (1) and more particularly the yield and purity of formula (1a) when $R_3$=$CH_3$, were widely variable and dependant on operational conditions and the quality of the products and reagents used. Thus, the reaction sequence used was not reproducible. As a result of the nature of some of the reagents used (e.g., oxalyl chloride and dichloromethane), some of the by-products formed (e.g., dimethylsulfide) and the complexity of the experimental protocol (e.g., very low temperature and sequential addition of several compounds perhaps in excess), this reaction sequence was extremely difficult to carry out technically, even impossible to carry out, on a semi-industrial or industrial scale.

The new method of the invention (cf. scheme II) offers the advantage, among others, of using only chemically and stereochemically stable compounds.

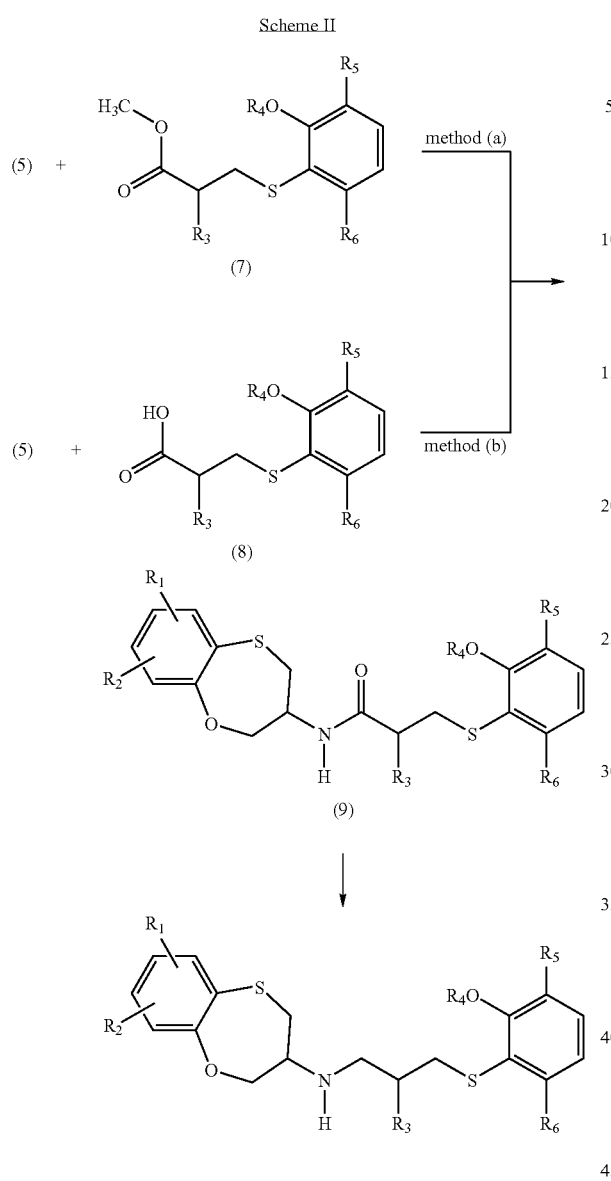

Scheme II

Thus:
according to method (a), the amine of formula (5) and the ester of formula (7) are condensed in the presence of an alkylaluminum derivative such as, for example, diisobutylaluminum hydride according to a method analogous to that reported in Tetrahedron Lett. 2001, 42(51), 9039-41.

According to method (b), the amine of formula (5) and the acid of formula (8) are condensed by means of a coupling agent such as, for example, carbonyl diimidazole according to a method analogous to that described in J. Org. Chem. 2003, 68(7), 2633-38.

The amide (9), formed by one of the methods (a) or (b), is generally a chemically and stereochemically stable crystalline compound that can, if desired, be purified by recrystallization. The formula (9) compound is then reduced, without loss of stereochemical purity, to a formula (1) amine by means of a borane complex such as, for example, the complex borane-THF. Next, the formula (1) compound can be salified, if desired, by means of a pharmaceutically acceptable organic or inorganic acid. The new method is thus reproducible, robust, and can be carried out on a semi-industrial or industrial scale.

An additional aspect of the present invention comprises the improvement of the method of synthesis of the formula (5) amine.

In the patent application WO 02/081464, the synthesis of compound (5) used an appropriate 2-hydroxy-benzenethiol and N-Boc-L-serine as raw materials. The synthesis of compound (5), according to the suggested approach, then included five steps of which two called upon Mitsunobu-type reactions and one involved the hydrolysis of a protecting group. However, the two Mitsunobu-type reactions generated quantities of non-recyclable by-products (i.e., triphenylphosphine oxide and alkyl hydrazinodicarboxylate) that were much greater than that of the target product (>400% in weight), and which were difficult to separate from the target product. Moreover, one of the reagents used (i.e., alkyl diazodicarboxylate) is known for its instability. The deprotection of the primary amine function, in the last step, also caused a significant loss (>50%) of formula (5) compound weight. Finally, starting products such as 2-hydroxy-benzenethiols are, generally, strongly odorous, and difficult to obtain and/or to keep pure because they are easily oxidizable. In terms of economy of atoms, treatment of effluent, and thus the cost price, the preparation of amine (5) according to the method described in patent application WO 02/081464 presents a very unfavorable balance. By comparison, the preparation of formula (5) amine according to the method of the invention is far more advantageous (cf. scheme III).

Scheme III

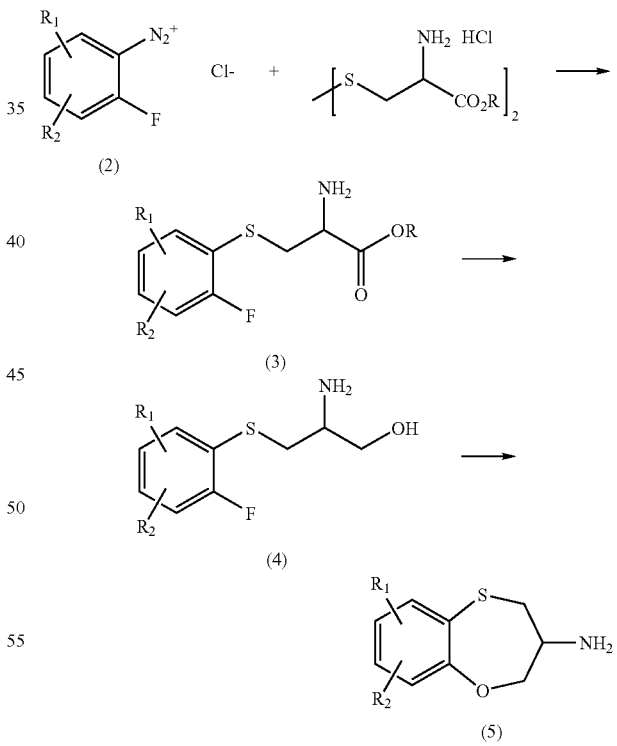

Thus, the reaction of L-cystine dimethylester [32854-09-4] with an appropriate formula (2) diazonium salt, according to a method analogous to that described in U.S. Pat. No. 5,599,992, leads to the formula (3) compound. This methodology, although classical organic chemistry (e.g., WO 00/39079), has never been applied in the case of a cystine diester. The formula (3) amino-ester is not purified but rather reduced to the formula (4) amino-alcohol by means of a hydride donor agent such as, for example, lithium-aluminum hydride. The compound is not purified but cyclized, chemoselectively, into the formula (5) amine. The said amine (5) can be used as such in the following reaction, or salified, by example, into the form of a chlorhydrate. The formula (5) amine or its chlorhydrate can be used in the coupling reaction with the compounds of formulas (7) and (8), cf. example 4, method (c). Thus according to the invention, access to the formula (5) compound requires fewer steps and proceeds with a higher yield than the method proposed in WO 02/081464. The new method also makes it possible to avoid the disadvantages inherent in the previous method, such as the use of relatively inaccessible raw materials, costly reagents, the formation of large quantities of by-products, and the use of the protecting group.

An additional aspect of the invention includes the method for preparing new intermediates of formulas (7) and (8), cf. scheme IV.

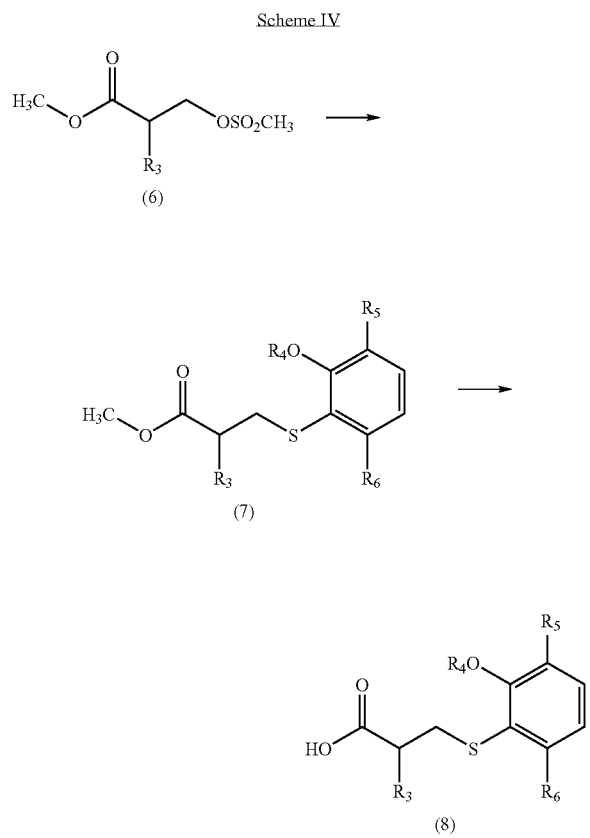

Thus, the alcohol function of methyl 3-hydroxy-2-alkyl-propanoate is first activated in the form of a mesylate of the formula then displaced by the appropriate thiophenol to yield formula (7) compound. The formula (7) compound can be:
  either engaged directly in a condensation reaction with the amine, method (a), scheme II;
  or hydrolyzed in the acid corresponding to formula (8) then engaged in the condensation reaction with amine (5), method (b), scheme II.
The said acid (8) is crystalline, chemically and stereochemically stable, and can be purified by recrystallization if desired, which can be advantageous in certain specific cases.

The following examples illustrate the invention without, however, limiting its scope.

EXAMPLE 1

(3R)-3,4-dihydro-2H-1,5-benzoxathiepin-3-amine (5a-1) [470662-82-9]

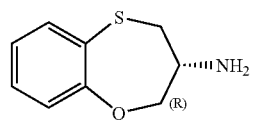

Step 1: 2-fluorobenzenediazonium (2a-1) [45660-02-4]

In a round-bottom flask, 4.1 mL (48.8 mmoles) of 36% hydrochloric acid is added to a solution of 2.36 mL (24.4 mmoles) of fluoroaniline in 15 mL of distilled water. The reaction medium is brought to 60° C. for 15 minutes then cooled to 0° C. Then a solution of 1.68 g (24.4 mmoles) of sodium nitrite dissolved in 10 mL of distilled water is added dropwise. The temperature of the mixture is maintained between 2° C. and 5° C. during the addition and then the mixture is stirred for 15 minutes after the addition is completed. The homogeneous aqueous solution containing compound (2a-1) is used directly in the following step.

Step 2: Methyl S-(2-fluorophenyl)-L-cysteinate (3a-1)

The aqueous solution containing the diazonium salt (2a-1) obtained in step 1 is added dropwise (approximately 30 minutes) to a solution of 4.16 g (12.2 mmoles) of L-cystine dimethylester dichlorohydrate and 328 mg (2.44 mmoles) of $CuCl_2$ in 19 mL of distilled water maintained between 50° C. and 55° C. The heterogeneous reaction medium is stirred for 5 minutes after gas release is complete then cooled to ambient temperature and washed with ethylic ether. The aqueous phase is neutralized by the addition of a 32% (5.6 mL, 94 mmoles) aqueous ammonia solution then extracted with ethyl acetate. The combined organic phases are washed with a 10% sodium bisulfite solution then with brine, dried over sodium sulfate, filtered, and concentrated under reduced pressure. A brown oil (3.7 g) is obtained that can be used without any additional purification in the following step.
$^1$H NMR ($CDCl_3$) δ: 1.69 (1s, 2H exchangeable); 3.15 (dd, 1H); 3.30 (dd, 1H); 3.60 (s, 3H); 3.62 (m, 1H); 7.08 (d, 1H); 7.12 (d, 1H); 7.26 (m, 1H); 7.46 (dd, 1H);
IR (slides) ν: 1739 $cm^{-1}$.

Step 3: (2R)-2-amino-3-[(2-fluorophenyl)sulfanyl]propan-1-ol (4a-1)

In a round-bottom flask maintained under an inert atmosphere, 23.9 mL (23.9 mmoles) of lithium aluminum hydride (1M in THF) is introduced. The solution is cooled to 0° C. then 4.57 g (19.9 mmoles) of methyl S-(2-fluorophenyl)-L-cysteinate (3a-1) diluted in 21 mL of anhydrous THF is added. The solution is stirred at 0° C. for 1 hour then at ambient temperature for 30 minutes. The reaction medium is hydrolyzed by successive additions of 2.7 mL of water, 0.9 mL of 15% soda in water, then 0.9 mL of water. The suspension is stirred for 30 minutes at ambient temperature in the presence of sodium sulfate then filtered on a silica filter. The precipitate is washed with THF then the filtrate is concentrated under reduced pressure. A brown oil (3.56 g) is obtained that can be used without any additional purification in the following step.

$^1$H NMR (CDCl$_3$) δ: 1.45 (1s, 2H exchangeable); 1.86 (m, 1H); 2.79 (dd, 1H); 3.08 (dd, 1H); 3.43 (dd, 1H); 3.64 (dd, 1H); 3.75 (m, 1H); 7.06 (d, 1H); 7.10 (d, 1H); 7.25 (m, 1H); 7.42 (dd, 1H).

Step 4: (3R)-3,4-dihydro-2H-1,5-benzoxathiepin-3-amine (5a-1) [470662-82-9]

In a round-bottom flask maintained under an inert atmosphere, 3.55 g (17.6 mmoles) of (2R)-2-amino-3-[(2-fluorophenyl)sulfanyl]propan-1-ol (4a-1) and 71 mL of dioxane are introduced. The solution is cooled to 0° C. then 9.90 g (88.2 mmoles) of potassium tert-butylate is added in portions, followed by stirring at ambient temperature for 12 hours. The mixture is then concentrated under reduced pressure and the residue taken up with water then extracted with ethyl acetate. The combined organic phases are washed with water, then brine, dried over sodium sulfate, filtered, and concentrated under reduced pressure. The brown oil thus obtained is taken up with a solution of 2.2 N HCl in ethanol (10.9 mL). The mixture is concentrated under reduced pressure and the chlorhydrate of the title compound is precipitated with the addition of isopropyl ether. The solid is filtered, washed with isopropyl ether, then dried under vacuum. The chlorhydrate of the title compound is obtained in the form of a solid cream (2.73 g, 12.5 mmoles).

Yield over 4 steps: 51%;
F=235° C.;
[α]=+48.9 (c=0.350, methanol);
$^1$H NMR (CDCl$_3$) δ: 1.69 (1s, 2H exchangeable); 2.77 (dd, 1H); 3.17 (dd, 1H); 3.42 (m, 1H); 4.07 (dd, 1H); 4.12 (dd, 1H); 6.96 (m, 2H); 7.14 (dt, 1H); 7.36 (dd, 1H).
$^1$H NMR (DMSO-d$_6$) δ: 3.12 (dd, 1H); 3.21 (dd, 1H); 3.81 (m, 1H); 4.21 (dd, 1H); 4.31 (dd, 1H); 7.09 (m, 2H); 7.28 (td, 1H); 7.45 (dd, 1H); 8.64 (1s, 3H exchangeable).

EXAMPLE 2

Methyl (2S)-3-[(2-methoxyphenyl)sulfanyl]-2-methylpropanoate (7a-1)

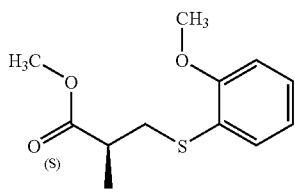

Step 1: Methyl (2R)-2-methyl-3-[(methylsulfonyloxy]propanoate (6a-1)

In a round-bottom flask maintained under an inert atmosphere, 4 g (33.9 mmoles) of methyl (2R)-3-hydroxy-2-methylpropanoate, 5.43 mL (38.9 mmoles) of triethylamine, 4.68 g (33.9 mmoles) of potassium carbonate, and 40 mL of anhydrous THF are introduced. To this solution maintained 0° C., 2.88 mL (37.2 mmoles) of methanesulfonyl chloride is added and the mixture is stirred at ambient temperature for 12 hours. The white precipitate that is formed is filtered, rinsed with THF, and the filtrate is then concentrated under reduced pressure. The residue is taken up with ethylic ether and the organic phase is washed with water until the wash water is neutral. The organic phase is washed with brine, dried over sodium sulfate, filtered, and concentrated under reduced pressure. The title compound is obtained in the form of a colorless oil (5.13 g) that can be used without any additional purification in the following step.

$^1$H NMR (CDCl$_3$) δ: 1.26 (d, 3H); 2.90 (m, 1H); 3.03 (s, 3H); 3.74 (s, 3H); 4.27 (dd, 1H); 4.38 (dd, 1H);
IR (slides) ν: 966, 1736 cm$^{-1}$.

Step 2: Methyl (2S)-3-[(2-methoxyphenyl)sulfanyl]-2-methylpropanoate (7a-1)

In a round-bottom flask maintained under an inert atmosphere, 4.72 mL (38.8 mmoles) of 2-methoxythiophenol, 10.72 g (77.6 mmoles) of potassium carbonate, 5.13 g of diluted methyl (2R)-2-methyl-3-[(methylsulfonyl)oxy]propanoate (6a-1) and 100 mL of anhydrous THF then 329 mg (0.97 mmole) of tetrabutylammonium hydrogen sulfate are introduced. The reaction medium is brought to 60° C. for 24 h under vigorous stirring then concentrated under reduced pressure. The residue is taken up with water and is extracted with ethylic ether. The combined organic phases are washed with a 1 N soda solution, water, brine, then dried over sodium sulfate, filtered, and concentrated under reduced pressure. The residue is taken up in methanol and concentrated then taken up again in methanol (10 mL/1 g of residue). The bis(methoxyphenyl) disulfide [13920-94-0] that slowly precipitates is eliminated by filtration. The filtrate is evaporated under reduced pressure to yield the title compound in the form of a pale yellow oil (6.4 g, 26.6 mmoles).

Yield over 2 steps: 69%;
[α]=−71.6 (c=0.173, methanol);
$^1$H NMR (CDCl$_3$); 1.28 (d, 3H); 2.67 (m, 1H); 2.88 (dd, 1H); 3.25 (dd, 1H); 3.66 (s, 3H); 3.89 (s, 3H); 6.86 (d, 1H); 6.91 (dd, 1H); 7.21 (dd, 1H); 7.32 (d, 1H);
IR (slides) ν: 1732 cm$^{-1}$;
HPLC, Chiralcel OD column (hexane/isopropanol 98:2, 1 mL/min): retention time Tr=13.28 min.

Step 3: (2S)-3-[(2-methoxyphenyl)sulfanyl]-2-methylpropanoic acid (8a-1)

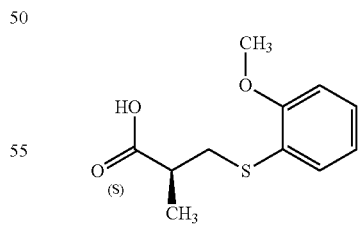

In a round-bottom flask, 7.11 g (29.6 mmoles) of methyl (2S)-3-[(2-methoxyphenyl)sulfanyl]-2-methylpropanoate (7a-1) and 35.5 mL of THF are introduced. 6.21 g (0.148 mole) of LiOH.H$_2$O dissolved in 35.5 mL of water is added. The mixture is stirred at 50° C. for 12 hours then concentrated under reduced pressure. The residue is taken up with water and the extract is taken up with toluene. The aqueous phase is acidified (pH=2) by adding 36% hydrochloric acid and then extracted with ethyl acetate. The combined organic phases are washed with brine, dried over sodium sulfate, and concentrated under reduced pressure. The title compound is obtained in the form of a white solid, (5 g, 22.1 mmoles) that can be recrystallized in isopropyl ether if desired.

Yield over 3 steps: 65%;
F=103° C.;
[α]=−41.5 (c=0.492, methanol);
$^1$H NMR (CDCl$_3$) δ: 1.31 (d, 3H); 2.69 (m, 1H); 2.88 (dd, 1H); 3.27 (dd, 1H); 6.86 (d, 1H); 6.91 (dd, 1H); 7.22 (dd, 1H); 7.34 (d, 1H); 10.85 (ls, 1H exchangeable);
IR (KBr) ν: 1720, 3114 cm$^{-1}$;
HPLC, Chiralcel OD column (hexane/ethanol/TFA 95:5:0.5, 1 mL/min): Tr=14.57 min.

| C$_{11}$H$_{14}$O$_3$S analysis: | | |
|---|---|---|
| Calc. % | C58.38 | H6.24 |
| Tr. | C58.41 | H6.32 |

EXAMPLE 3

Methyl (2R)-3-[(2-methoxyphenyl)sulfanyl]-2-methylpropanoate (7a-2)

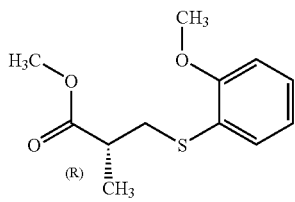

Step 1: Methyl (2R)-3-[(2-methoxyphenyl)sulfanyl]-2-methylpropanoate (7a-2)

By proceeding as in example 2, step 2, but using methyl (2S)-2-methyl-3-[(methylsulfonyl)oxy]propanoate [142402-78-6] in the place of methyl (2R)-2-methyl-3-[(methylsulfonyl)oxy]propanoate (6a-1), the title compound is obtained.
[α]=+67.1 (c=0.368, methanol);
HPLC, Chiralcel OD column (hexane/isopropanol 98:2, 1 mL/min): Tr=16.47 min.

Step 2: (2R)-3-[(2-methoxyphenyl)sulfanyl]-2-methylpropanoic acid (8a-2)

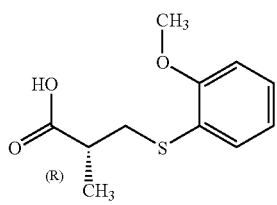

By proceeding as in example 2, step 3, but using methyl (2R)-3-[(2-methoxyphenyl)sulfanyl]-2-methylpropanoate (7a-2) in the place of methyl (2S)-3-[(2-methoxyphenyl)sulfanyl]-2-methylpropanoate (7a-1), the title compound is obtained.

[α]=+43.3 (c=0.455, methanol);
HPLC, Chiralcel OD column (hexane/ethanol/TFA 95:5:0.5, 1 mL/min): Tr=18.09 min.

EXAMPLE 4

(2S)-N-[(3R)-3,4-dihydro-2H-1,5-benzoxathiepin-3-yl]-3-[(2-methoxyphenyl)sulfanyl]-2-methylpropanamide (9a-1)

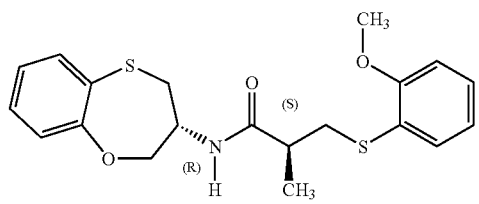

Method (a): The chlorhydrate of (3R)-3,4-dihydro-2H-1,5-benzoxathiepin-3-amine (1.5 g, 6.89 mmoles) is added at ambient temperature to a 10 N NaOH solution (10 mL). Next, the mixture is extracted with ethylic ether, the organic phase washed with salt water, dried over sodium sulfate, then concentrated under reduced pressure. The residue is taken up in dichloromethane or toluene and concentrated under vacuum. The amine (5a-1) is recovered in the form of a colorless oil (1.1 g, 6.07 mmoles) that is used in the following step without additional purification.

Yield: 88%;

In a round-bottom flask maintained under an inert atmosphere, 1.1 g of (3R)-3,4-dihydro-2H-1,5-benzoxathiepin-3-amine (6.07 mmoles) and 10 mL of THF are introduced. To this solution cooled to 0° C., a 1 M solution of diisopropylaluminum hydride in THF (6.7 mL, 6.7 mmoles) is added dropwise. When the release of gases has ceased, the reaction mixture is stirred at ambient temperature for 1 hour then cooled to 0° C. Methyl (2S)-3-[(2-methoxyphenyl)sulfanyl]-2-15 methylpropanoate (7a-1), 1.6 g, 6.67 mmoles, is added, then the mixture is heated at 50° C. for 12 hours. The reaction mixture is poured into a saturated aqueous Rochelle salt solution (70 mL) and the mixture is stirred until it becomes limpid. The mixture is extracted with ethyl acetate, the combined organic phases are washed with water then salt water, dried over sodium sulfate, then filtered and concentrated under reduced pressure. The residue is taken up with diisopropyl ether, concentrated, then taken up again with diisopropyl ether. The title compound then slowly crystallizes. The precipitate is filtered, washed with cold diisopropyl ether, and dried under vacuum. The title compound is obtained in the form of a white solid (1.3 g, 3.34 mmoles).

Yield: 55%;

Method (b): In a round-bottom flask maintained under an inert atmosphere, 200 mg (0.884 mmole) of (2S)-3-[(2-methoxyphenyl)sulfanyl]-2-methylpropanoic acid (8a-1) and 2 mL of anhydrous THF are introduced. Next, 148 mg (0.91 mmole) of N,N'-carbonyldiimidazole is added in portions. The mixture is stirred at ambient temperature for 3 hours then 160 mg (0.884 mmole) of (3R)-3,4-dihydro-2H-1,5-benzoxathiepin-3-amine (5a-1) dissolved in 1.5 mL of anhydrous THF is added. The solution is stirred at ambient temperature for 12 hours. The mixture is hydrolyzed with 2 mL of a 3 M $H_3PO_4$ solution. The aqueous phase is extracted with ethyl acetate. The combined organic phases are washed with a 1 M $H_3PO_4$ solution, a saturated $NaHCO_3$ solution, water and brine, then dried over sodium sulfate, filtered, and concentrated under reduced pressure. The title compound is obtained in the form of a white solid (264 mg, 0.678 mmole).

Yield: 77%;

Method (c): In a round-bottom flask maintained under an inert atmosphere, 200 mg (0.884 mmole) of (2S)-3-[(2-methoxyphenyl)sulfanyl]-2-methylpropanoic acid (8a-1) and 3.5 mL of anhydrous THF are introduced. Next, 148 mg (0.91 mmole) of N,N'-carbonyldiimidazole is added in portions. The mixture is stirred at ambient temperature for 3 hours then 193 mg (0.884 mmole) of chlorhydrate of (3R)-3,4-dihydro-2H-1,5-benzoxathiepin-3-amine and 0.219 mL (1.33 mmoles) of diisopropylethylamine are added. The solution is stirred at ambient temperature for 12 hours. The reaction mixture is treated as in method (b) to yield the title compound (250 mg, 0.642 mmole).

Yield: 73%;
F=102° C.;
[α]=−46.14 (c=0.485, methanol);
$^1$H NMR ($CDCl_3$) δ: 1.28 (d, 3H); 2.50 (m, 1H); 2.93 (m, 2H); 3.03 (dd, 1H); 3.22 (dd, 1H); 3.89 (s, 3H); 3.92 (m, 1H); 4.32 (dd, 1H); 4.60 (m, 1H); 6.77 (ld, 1H); 6.95 (m, 4H); 7.20 (m, 2H); 7.37 (d, 1H); 7.44 (d, 1H);
IR (KBr) ν: 1640. 3278 $cm^{-1}$;

EXAMPLE 5

(3R)-N-{(2S)-3-[(2-methoxyphenyl)sulfanyl]-2-methylpropyl}-3,4-dihydro-2H-1,5-benzoxathiepin-3-amine (1a-1) [470-454-73-0]

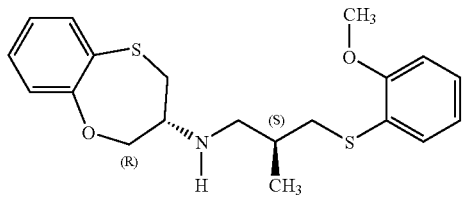

In a round-bottom flask maintained under an inert atmosphere, 250 mg (0.642 mmole) of (2S)-N-[(3R)-3,4-dihydro-2H-1,5-benzoxathiepin-3-yl]-3-[(2-methoxyphenyl)sulfanyl]-2-methylpropanamide (9a-1) and 7.5 mL of anhydrous THF are introduced. Next, 3.21 mL (3.21 mmoles) of 1 M $BH_3$.THF is added dropwise, then the solution is heated to reflux for 1 h 30 min. The mixture is cooled, concentrated under reduced pressure, taken up with 20 mL of methanol, then acidified with 36% hydrochloric acid. The mixture is brought to reflux for 4 hours then stirred for 12 hours at ambient temperature. The reaction mixture is concentrated under reduced pressure then made basic (pH=10) by adding concentrated soda. The aqueous phase is extracted with dichloromethane, the combined organic phases are washed with brine, dried over sodium sulfate, filtered, and concentrated under reduced pressure. The title compound is obtained in the form of a colorless oil (232 mg, 0.618 mmole).

Yield: 96%;
$^1$H NMR ($CDCl_3$) δ: 1.10 (d, 3H); 1.66 (ls, 1H exchangeable); 1.92 (m, 1H); 2.63 (dd, 1H); 2.77 (dd, 1H); 2.79 (dd, 1H); 2.94 (dd, 1H); 3.08 (dd, 1H); 3.10 (dd, 1H); 3.14 (m, 1H); 3.90 (s, 3H); 4.07 (dd, 1H); 4.24 (dd, 1H); 6.84 (d, 1H); 6.93 (d, 1H); 7.00 (m, 2H); 7.15 (m, 2H); 7.33 (m, 2H);

HPLC, Chiralcel OJ column, thermostated at 40° C. (methanol/ethanol/diethylamine 49.95:49.95:0.1, 1 mL/min):
Tr=25.11 min;

The optical purity of compound (1a-1), calculated from the ratios of the areas under the curve of the four stereoisomers, is 98.5% (diastereoisomeric excess=97%).

EXAMPLE 6

(3R)-N-{(2R)-3-[(2-methoxyphenyl)sulfanyl]-2-methylpropyl}-3,4-dihydro-2H-1,5-benzoxathiepin-3-amine (1a-2) [470-454-75-2]

HPLC, Chiralcel OJ column, thermostated at 40° C. (methanol/ethanol/diethylamine 49.95:49.95:0.1, 1 mL/min): Tr=16.89 min.

EXAMPLE 7

(3S)-N-{(2S)-3-[(2-methoxyphenyl)sulfanyl]-2-methylpropyl}-3,4-dihydro-2H-1,5-benzoxathiepin-3-amine (1a-3)

HPLC, Chiralcel OJ column, thermostated at 40° C. (methanol/ethanol/diethylamine 49.95:49.95:0.1, 1 mL/min): Tr=20.09 min.

EXAMPLE 8

(3S)-N-{(2R)-3-[(2-methoxyphenyl)sulfanyl]-2-methylpropyl}-3,4-dihydro-2H-1,5-benzoxathiepin-3-amine (1a-4)

HPLC, Chiralcel OJ column, thermostated at 40° C. (methanol/ethanol/diethylamine 49.95:49.95:0.1, 1 mL/min): Tr=14.94 min.

EXAMPLE 9

(3R)-N-{(2S)-3-[(2-methoxyphenyl)sulfanyl]-2-methylpropyl}-3,4-dihydro-2H-1,5-benzoxathiepin-3-amine, bromhydrate (1a-1b)

0.35 mL (3.0 mmoles) of a 48% HBr solution in water is added to a suspension of (3R)-N-{(2S)-3-[(2-methoxyphenyl)sulfanyl]-2-methylpropyl}-3,4-dihydro-2H-1,5-benzoxathiepin-3-amine (1 g, 2.66 mmoles) in 20 mL of water. The mixture is heated and acetone added until a homogeneous solution is obtained. The bromhydrate of the title compound that crystallizes during the cooling of the solution is filtered, washed with acetone, then dried under vacuum. The title compound is obtained in the form of a white solid (0.87 g, 1.91 mmoles).

Yield: 72%;
F=129-131° C.;
[α]=−9.6 (c=0.187, methanol);
$^1$H NMR (DMSO-$d_6$) δ: 1.12 (d, 3H), 2.19 (m, 1H), 2.82 (dd, 1H), 3.05 (lm, 1H), 3.12 (dd, 1H), 3.23 (lm, 1H), 3.32 (m, 2H), 3.82 (s, 3H), 3.90 (ls, 1H), 4.39 (dd, 1H), 4.52 30 (dd, 1H), 6.98 (m, 2H), 7.07 (m, 2H), 7.23 (m, 3H), 7.40 (dd, 1H), 8.88 (ls, 2H exchangeable);
$C_{20}H_{26}BrNO_2S_2$ analysis:

| C₂₀H₂₆BrNO₂S₂ analysis: | | |
|---|---|---|
| Calc. % C52.63 | H5.74 | N3.07 |
| Tr. C52.26 | H5.66 | N3.21 |

The optical purity of compound (1a-1b), calculated from the ratios of the areas under the curve is 99.2% (diastereoisomeric excess=98.4%).

The invention claimed is:

1. A method for preparing formula (1) benzoxathiepine derivatives

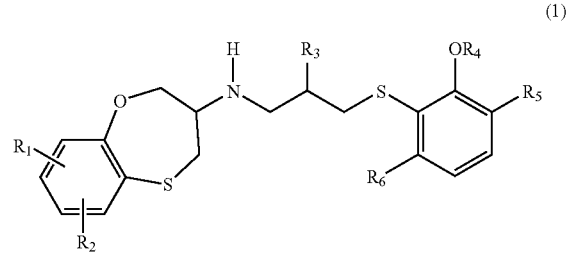
(1)

in which:

$R_1$ and $R_2$, identical or different, represent:

a hydrogen atom;

a fluorine atom or a chlorine atom;

a hydroxy group;

an alkyl radical, chosen from among the radicals methyl, ethyl, propyl, or isopropyl;

an alkoxy radical, chosen from among the radicals methoxy, ethyloxy, propyloxy, or isopropyloxy;

when groups $R_1$ and $R_2$ occupy adjacent positions on the aromatic ring, then $R_1R_2$ represents —CH₂CH₂CH₂—, —OCH₂CH₂—, —OCH₂O—, or —CH₂CH₂O—;

$R_3$ represents:

an alkyl radical, chosen from among the radicals methyl, ethyl, propyl, or isopropyl;

a hydroxy group or a methoxy radical;

$R_4$ represents:

a hydrogen atom or a methyl radical;

$R_5$ and $R_6$, identical or different, represent:

a hydrogen atom;

an alkyl radical, chosen from among the radicals methyl, ethyl, or isopropyl;

an alkoxy radical, chosen from among the radicals methoxy, ethyloxy, or isopropyloxy;

an alkylthio radical, chosen from among radicals methylthio, ethylthio, or isopropylthio;

an alkylamino radical, chosen from among the radicals N-methylamino or N,N-dimethylamino;

or $R_4R_5$ represents a radical chosen from among the radicals —CH₂CH₂—, —CH₂O—, —CH₂CH₂O—, —CH₂CH₂S—, —CH₂CH₂NR₄— and $R_6$ is as defined previously, characterized such that it is prepared by the reduction of an amide of formula (9)

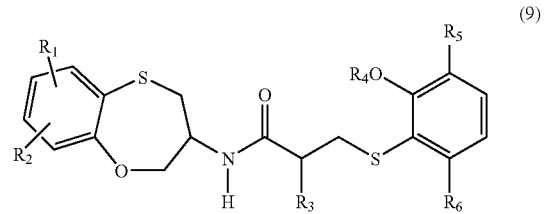
(9)

optionally obtained by condensation of the intermediates of formulae (5) and (7), or of the intermediates of formulae (5) and (8)

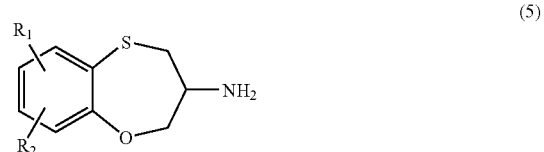
(5)

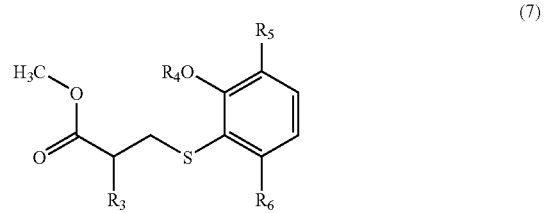
(7)

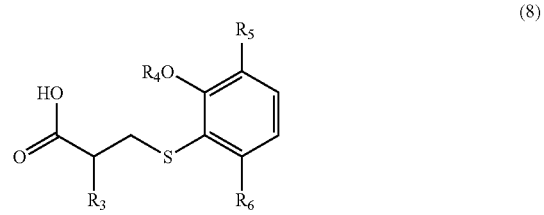
(8)

in which radicals $R_1$, $R_2$, $R_3$, $R_4$, $R_5$, and $R_6$ have the meaning given above with regard to formula (1).

2. A method according to claim 1, wherein the 3,4-dihydro-2H-1,5-benzoxathiepin-3-amines of formula (5)

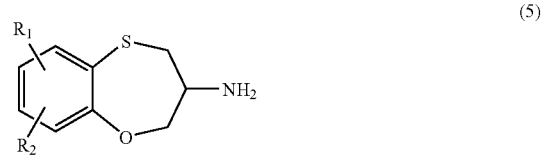
(5)

in which $R_1$ and $R_2$ have the meaning given in claim 1 with regard to formula (1) are prepared by carrying out the following reactions:

transformation of the diazonium salt of formula (2) into the alkyl S-(2-fluoroaryl)-cysteinate of formula (3) by means of a cystine ester

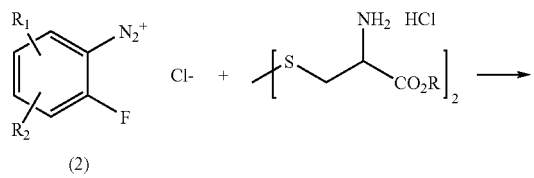

(2)

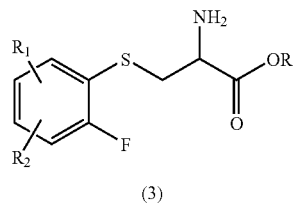

(3)

in which R represents a methyl radical, reduction of this compound by a hydride-donating agent to obtain the 2-amino-3-[(2-fluoroaryl)sulfanyl]propan-1-ol of formula (4)

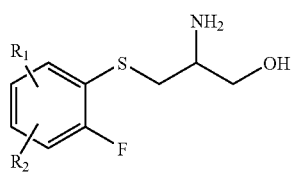

(4)

chemoselective cyclization of this compound to yield the 3,4-dihydro-2H-1,5-benzoxathiepin-3-amines of formula (5) in which radicals R₁ and R₂ have the meaning given with regard to formula (1).

3. A method according to claim 1, wherein the intermediates of formula (7)

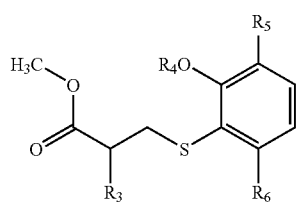

(7)

are prepared by the reaction of a formula (6) derivative of the type with 3-[(methylsulfonyl)oxy]propanoate substituted in position 2, with an appropriate arylthio phenol to yield the compound of formula (7)

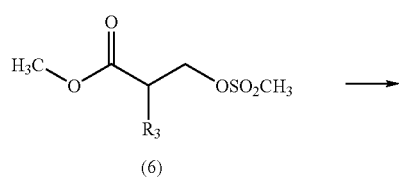

(6)

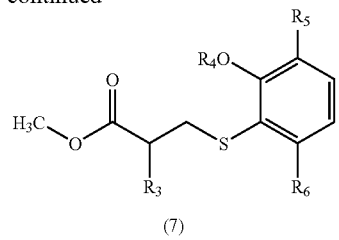

(7)

in which radicals R₃, R₄, R₅, and R₆ have the meaning given with regard to formula (1).

4. A method according to claim 1, wherein the intermediates of formula (8)

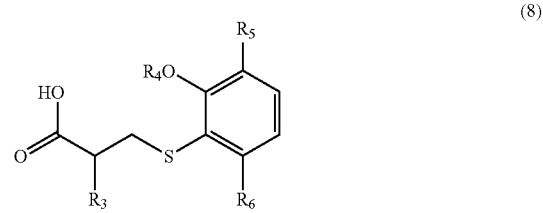

(8)

are prepared by the hydrolysis of a compound of formula (7) in a basic mixture to yield the acid corresponding to formula (8)

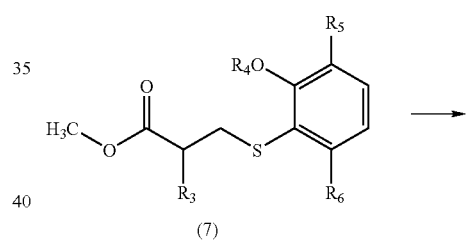

(7)

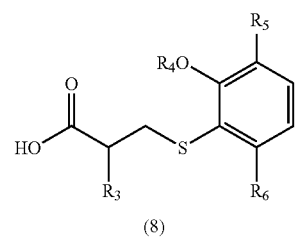

(8)

in which radicals R₃, R₄, R₅, and R₆ have the meaning given with regard to formula (1).

5. Synthetic intermediates of formula (9)

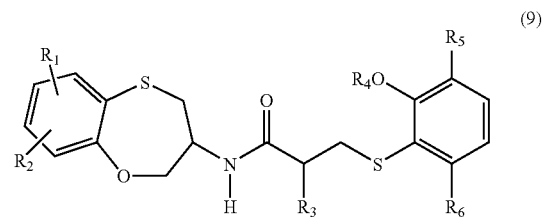

(9)

wherein $R_1$, and $R_2$, identical or different, represent:

a hydrogen atom;

a fluorine atom or a chlorine atom;

a hydroxy group;

an alkyl radical, chosen from among the radicals methyl, ethyl, propyl, or isopropyl;

an alkoxy radical, chosen from among the radicals methoxy, ethyloxy, propyloxy, or isopropyloxy;

when groups $R_1$ and $R_2$ occupy adjacent positions on the aromatic ring, then $R_1R_2$ represents —$CH_2CH_2CH_2$—, —$OCH_2CH_2$—, —$OCH_2O$—, or —$CH_2CH_2O$—;

$R_3$ represents:

an alkyl radical, chosen from among the radicals methyl, ethyl, propyl, or isopropyl;

a hydroxy group or a methoxy radical;

$R_4$ represents:

a hydrogen atom or a methyl radical;

$R_5$ and $R_6$, identical or different, represent:

a hydrogen atom;

an alkyl radical, chosen from among the radicals methyl, ethyl, or isopropyl;

an alkoxy radical, chosen from among the radicals methoxy, ethyloxy, or isopropyloxy;

an alkylthio radical, chosen from among radicals methylthio, ethylthio, or isopropylthio;

an alkylamino radical, chosen from among the radicals N-methylamino or N,N-dimethylamino.

6. A method for preparing formula (1a) compounds

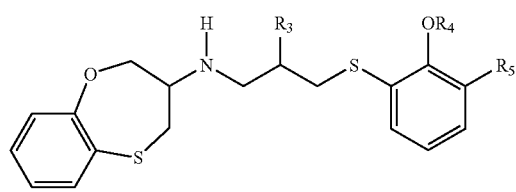
(1a)

in which:

$R_3$ represents an alkyl radical chosen from among the radicals methyl, ethyl, or isopropyl;

$R_4$ represents a hydrogen atom or a methyl radical;

$R_5$ represents a hydrogen atom or a methyl radical;

or $R_4R_5$ represents a —$CH_2CH_2$— radical comprising the reduction of an amide of formula (9a)

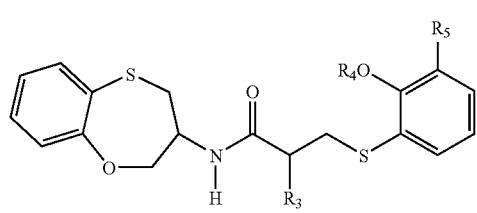
(9a)

optionally obtained by condensation of the intermediates of formulae (5a) and (7a), or of the intermediates of formulae (5a) and (8a)

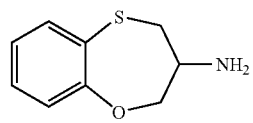
(5a)

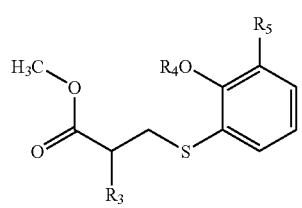
(7a)

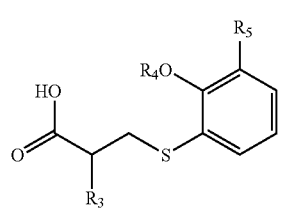
(8a)

in which radicals $R_3$, $R_4$, and $R_5$ have the meaning given above with regard to formula (1a).

7. A method according to claim 6, wherein the 3,4-dihydro-2H-1,5-benzoxathiepin-3-amines of formula (5a)

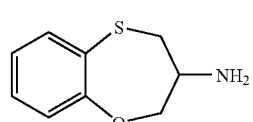
(5a)

are prepared by carrying out the following reactions:

transformation of the formula (2) diazonium salt into a S-(2-fluorophenyl)-cysteinate alkyl of formula (3a) by means of a cystine ester

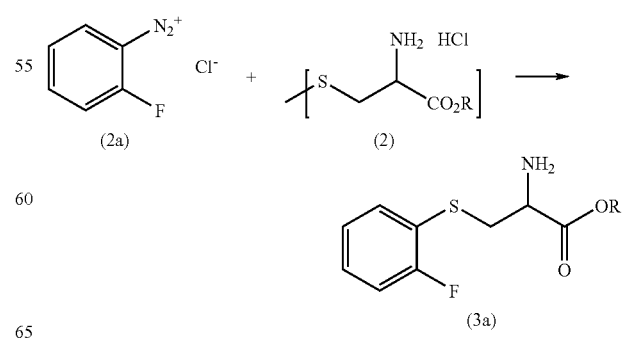

reduction of this compound by a hydride-donating agent to obtain the 2-amino-3-[(2-fluorophenyl)sulfanyl]propan-1-ol of formula (4a)

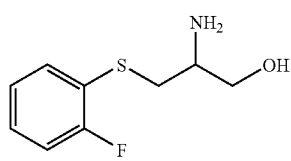

(4a)

cyclization of this compound in a basic mixture to yield the 3,4-dihydro-2H-1,5-benzoxathiepin-3-amines of formula (5a).

8. A method according to claim 6, wherein the intermediates of formula (7a)

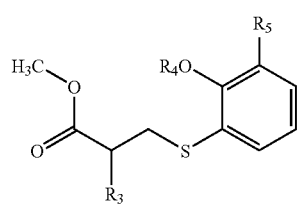

(7a)

are prepared by the reaction of a formula (6) derivative of the type with 3-[(methylsulfonyl)oxy]propanoate substituted in position 2, with an appropriate arylthio phenol to yield the compound of formula (7a)

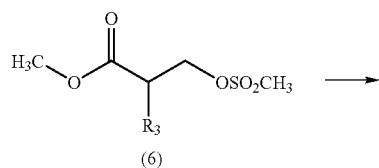

(6)

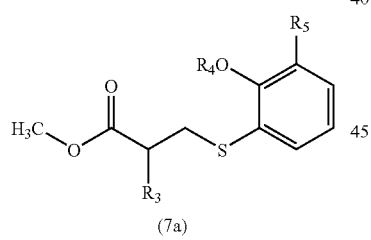

(7a)

in which radicals $R_3$, $R_4$, and $R_5$ have the meaning given with regard to formula (1a).

9. A method according to claim 6, wherein the intermediates of formula (8a)

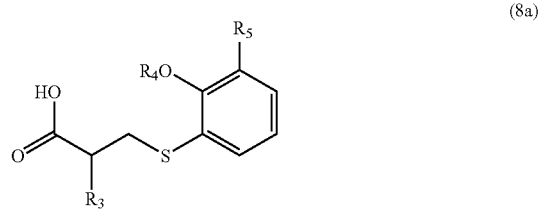

(8a)

are prepared by the hydrolysis of a compound of formula (7a) in a basic mixture to yield the acid corresponding to formula (8a)

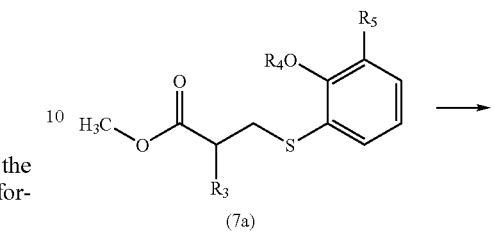

(7a)

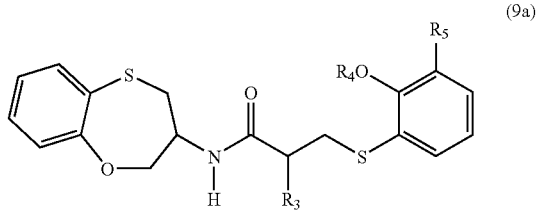

(8a)

in which radicals $R_3$, $R_4$, and $R_5$ have the meaning given with regard to formula (1a).

10. Synthetic intermediates of formula (9a)

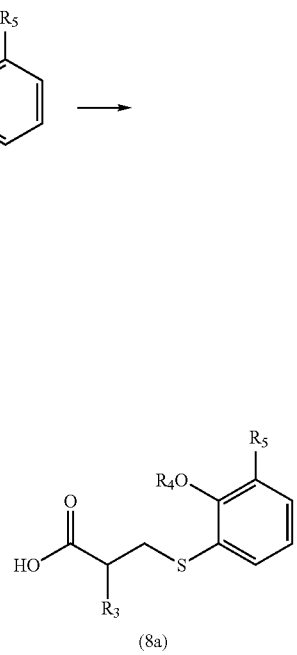

(9a)

wherein $R_3$ represents an alkyl radical chosen from among the radicals methyl, ethyl, or isopropyl;

$R_4$ represents a hydrogen atom or a methyl radical;

$R_5$ represents a hydrogen atom or a methyl radical.

11. A method for preparing derivatives of benzoxathiepines of general formulas (1) and (1a), according to one of the claims 1 and 6, wherein the compounds of formula (1) or (1a), in which the stereogenic C(3) carbon atom of fragment 3,4-dihydro-2H-1,5-benzoxathiepine is of absolute configuration (R) and the stereogenic carbon atom that carries the $R_3$ group is of absolute configuration (S), are prepared.

12. Intermediate compounds of formulas (9) and (9a) according to one of claims 5 and 10 in which the stereogenic C(3) carbon atom of fragment 3,4-dihydro-2H-1,5-benzoxathiepine is of absolute configuration (R) and the stereogenic carbon atom that carries the $R_3$ group is of absolute configuration (S).

13. Intermediate compounds of formulas (7) or (7a)

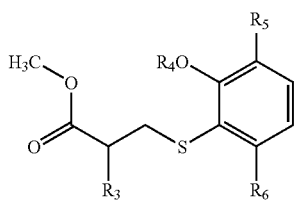

(7)

wherein $R_3$ represents:

an alkyl radical, chosen from among the radicals methyl, ethyl, propyl, or isopropyl;

a hydroxy group or a methoxy radical;

$R_4$ represents:

a hydrogen atom or a methyl radical;

$R_5$ and $R_6$, identical or different, represent:

a hydrogen atom;

an alkyl radical, chosen from among the radicals methyl, ethyl, or isopropyl;

an alkoxy radical, chosen from among the radicals methoxy, ethyloxy, or isopropyloxy;

an alkylthio radical, chosen from among radicals methylthio, ethylthio, or isopropylthio;

an alkylamino radical, chosen from among the radicals N-methylamino or N,N-dimethylamino;

$R_3$ being other than a methyl radical when $R_4$ and $R_5$ each represent a hydrogen atom

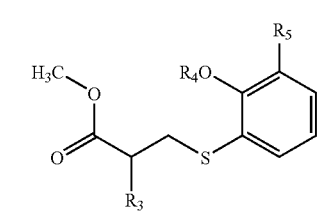

(7a)

wherein $R_3$ represents an alkyl radical chosen from among the radicals methyl, ethyl, or isopropyl;

$R_4$ represents a hydrogen atom or a methyl radical;

$R_5$ represents a hydrogen atom or a methyl radical;

$R_3$ being other than a methyl radical when $R_4$ $R_5$ and $R_6$ each represent a hydrogen atom in which the stereogenic carbon atom that carries the $R_3$ group is of absolute configuration (S).

14. Intermediate compounds of formulas (8) or (8a)

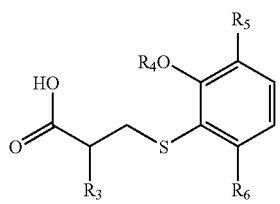

(8)

wherein $R_3$ represents:

an alkyl radical, chosen from among the radicals methyl, ethyl, propyl, or isopropyl;

a hydroxy group or a methoxy radical;

$R_4$ represents:

a hydrogen atom or a methyl radical;

$R_5$ and $R_6$, identical or different, represent:

a hydrogen atom;

an alkyl radical, chosen from among the radicals methyl, ethyl, or isopropyl;

an alkoxy radical, chosen from among the radicals methoxy, ethyloxy, or isopropyloxy;

an alkylthio radical, chosen from among radicals methylthio, ethylthio, or isopropylthio an alkylamino radical, chosen from among the radicals N-methylamino or N,N-dimethylamino;

(8a)

wherein $R_3$ represents an alkyl radical chosen from among the radicals methyl, ethyl, or isopropyl;

$R_4$ represents a hydrogen atom or a methyl radical;

$R_5$ represents a hydrogen atom or a methyl radical;

in which the stereogenic carbon atom that carries the $R_3$ group is of absolute configuration (S).

15. Method according to claim 6, wherein the following compounds are prepared:

N-{3-[(2-Methoxyphenyl)sulfanyl]-2-methylpropyl}-3,4-dihydro-2H-1,5-benzoxathiepin-3-amine;

2-{[3-(3,4-Dihydro-2H-1,5-benzoxathiepin-3-ylamino)-2-methylpropyl]sulfanyl}-6-methylphenol, (3R)-N-{(2S)-3-[(2-Methoxyphenyl)sulfanyl]-2-methylpropyl}-3,4-dihydro-2H-1,5-benzoxathiepin-3-amine;

2-({(2S)-3-[(3R)-3,4-Dihydro-2H-1,5-benzoxathiepin-3-ylamino]-2-methylpropyl}sulfanyl)-6-methylphenol, their addition salts and the hydrates of these addition salts with mineral acids or pharmaceutically acceptable organic acids.

* * * * *